United States Patent [19]

Brown

[11] Patent Number: 4,757,018

[45] Date of Patent: Jul. 12, 1988

[54] MYELOMA CELL LINES AND USES THEREOF

[75] Inventor: Bruce L. Brown, Knoxville, Md.

[73] Assignee: Hazleton Biotechnologies, Inc., Vienna, Va.

[21] Appl. No.: 700,199

[22] Filed: Feb. 11, 1985

[51] Int. Cl.$^4$ .................. C12N 5/00; C12N 15/00
[52] U.S. Cl. ...................... 435/240.2; 435/172.2; 435/240.27; 435/240.25; 435/240.31; 935/104
[58] Field of Search ............. 435/240, 241, 245, 948, 435/240.2, 240.21, 240.25, 240.26, 240.27, 240.3, 240.31, 172.1, 172.2; 935/89, 90, 92, 93, 95, 99, 100, 102–104, 108

[56] References Cited

U.S. PATENT DOCUMENTS

| | | | |
|---|---|---|---|
| Re. 30,985 | 7/1982 | Cartaya | 435/240.31 |
| 4,350,683 | 4/1982 | Galfre | 435/240.27 |
| 4,382,326 | 9/1981 | Moldenhauer | 435/240.31 |
| 4,438,032 | 7/1984 | Golde | 435/240.2 |
| 4,473,647 | 9/1984 | Carpenter | 435/240 |
| 4,533,637 | 8/1985 | Yamane | 435/240 |
| 4,560,655 | 12/1985 | Baker | 435/241 |

FOREIGN PATENT DOCUMENTS 0062409 10/1982 European Pat. Off. .

OTHER PUBLICATIONS

Murakami, H. et al., Anal. Biochem. 114(2):422-8(1981) cited in Chem Abstract CA95(11):93344q.
Murakami, H. et al., Agricul. Biol. Chem. 46(7):1831-7(1982) cited in Chem Abstract CA97(11):88232p.
Murakami, H. et al., Proc. Natl. Acad. Sci., U.S.A., 79: 1158-62(1982).
Ham, R. G., Growth of Cells in Hormonally Defined Media, Cold Spring Harbor (1982), vol. 9, Sato et al., eds. pp. 42-60.
Rossi, C. R. et al., Amer. J. Vet. Res., 41:1680-1 (10-1980).
Chu, F. C. et al., In Vitro, 9(1):31-34 (1973).
Nuttall, P. A. et al., Nature, 266:835-837 (4–1977).
Orr, H. C. et al., J. Clin. Microbiol, 3:402-5 (1976).
Abstract 123, Brown et al., In Vitro (Mar. 1984).
Kawamoto et al., Hormonally Defined Media: Tool Cell Biol, 1 Meet. 310-13 (1983).
Bezkorovainy and Zchocke, Arzheim-Forsch. (Drug. Res.) 24: 476-85 (1974).
Tormey et al., Exper. Cell Res., 74: 163 (1972).
Vogt et al., Exper. Cell Res. 54: 195 (1969).
Hayashi and Sato, Nature, 359: 132-34 (1976).
Guilbert and Iscove, Nature, 263: 594-95 (1976).
Iscove and Melchers, J. Exper. Med., 147: 923-933 (1978).
Ventrex HL-1 Circular, Copyright 1984.
Kearney et al., J. Immunol., 123: 1548-50 (1979).
Koprowski et al., PNAS (U.S.A.), 74: 2985-88 (1977).
Chang et al., J. Immunol. Meth., 39: 369-75 (1980).

*Primary Examiner*—Margaret Moskowitz
*Attorney, Agent, or Firm*—Iver P. Cooper

[57] ABSTRACT

Myeloma cell lines adapted for growth and cloned in a serum-free medium in which human transferrin is the sole protein source are described. These cells may be fused to immunocytes to create monoclonal antibody-secreting hybridomas in the same medium.

2 Claims, 1 Drawing Sheet

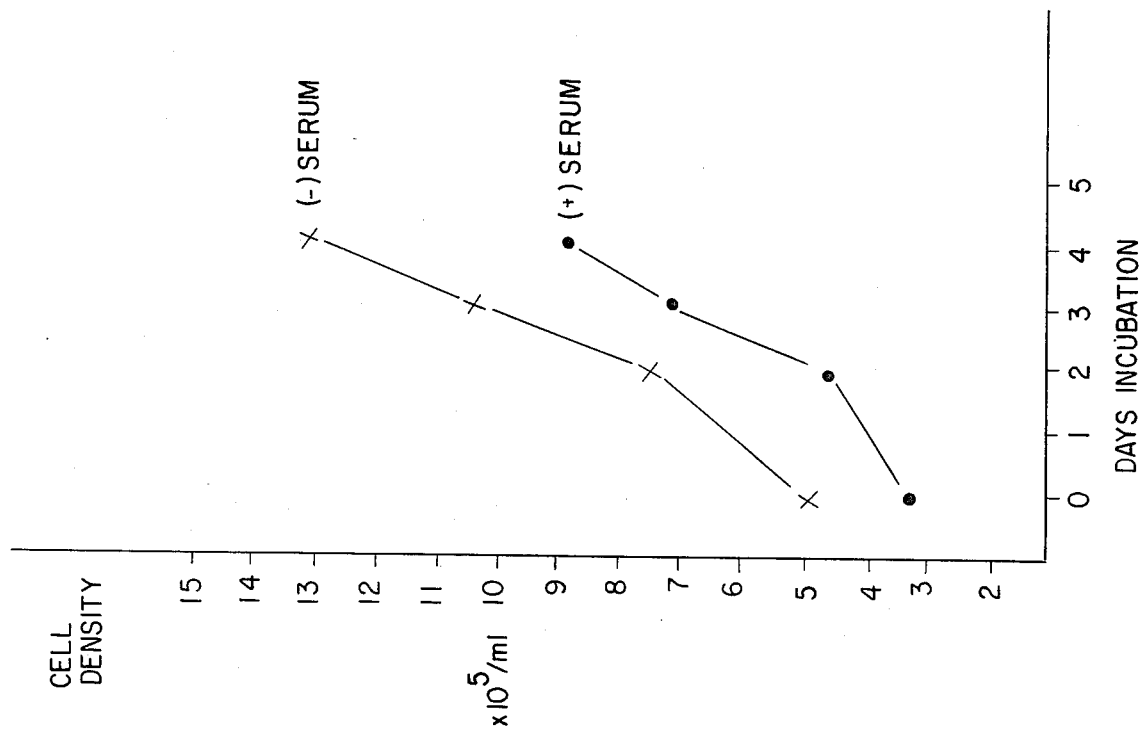

MYELOMA CELL LINES AND USES THEREOF

BACKGROUND OF THE INVENTION

This invention relates to myeloma cell lines adapted for growth and cloned in a serum-free medium in which transferrin is the sole protein supplement. Such cell lines may be used in the construction of hybridomas by fusion with immunocytes, e.g. splenocytes.

The development of somatic-cell hybrids as introduced by Kohler and Milstein in 1975, allows for the production of monoclonal antibodies with a desired specificity. These antibodies are functionally homogeneous, which greatly facilitates the standardization of immunochemical procedures and assures reproducibility in established assay systems. It is often necessary to obtain these antibodies in a highly purified state. One approach is to cultivate the antibody secreting hybrid cells in a chemically defined medium; that is, one free from any type of serum or serum supplement.

Serum is a very complex fluid, containing at least 500 different protein components with a total protein concentration approaching 150 mg/ml. Hybridoma culture medium is routinely supplemented with 5%-20% serum. This introduces a tremendous excess of heterologous protein beyond monoclonal antibody protein concentration, typically 1–100 mg/ml. The advantage of producing monoclonal antibodies in a serum-free system is evident strictly from a purification standpoint. Serum components may, however, interfere with assays for antibody reactivity, and, in any event, add considerably to the cost of the medium.

In attempting to develop serum-free cell lines, others have liberally added a variety of protein supplements, such as insulin, to minimal growth media. These supplemented media partake to some degree of the disadvantages of serum media because their protein components may be difficult to obtain free of contaminants, and to separate from the desired antibody product.

Rossi, et al., Am J. Vet. RES., 41:1680–1681 (1980); Chu, et al., In Vitro, 9:31–34 (1973); and Nuttall, et al., Nature, 266:835–837 (1977) all address the problem of viral contamination of serum. These viruses may interact biologically with mammalian cells in culture, as noted by Chu, or obscure clinical reactions to other agents, as observed by Nuttall.

A nubmer of techniques have been employed to alleviate viral contamination. These include regular screening of cell cultures, and removal of the viruses by affinity chromatography. Unfortunately, as reported by Orr, et al., J. Clin. Microbiol., 3:402–5 (1976), it is difficult to assure the elimination of all the different types of undesirable agents that may be present in a contaminated culture.

In contrast, we have found transferrin to be a well characterized and easily purified protein.

Work relating to the present invention was described in Abstract No. 123, Brown, Shriver, Harshman and Rener, Adaptation of a Murine Myeloma Cell Line to Serum-Free Media and Its Use as a Fusion Partner in Monoclonal Antibody Production, In Vitro (March 1984). The abstract, while mentioning use of transferring, does not state it was the sole protein source.

Kawamoto, et al., Hybridoma Formation in Serum-Free Medium in Hormonally Defined Media: Tool Cell (Biol (1983) 1 Meet. 310–13, abstracted in Derwent Biotechnology Abstracts, 84-06338 (July 2, 1984), describes a multipart basal medium (RPMI, Ham's F-12, and DME, combined) with many supplements (insulin, human transferrin, 2-aminoethanol, 2-mercaptoethanol, sodium selenite, human low density lipoprotein, oleic acid, and fatty acid-free bovine serum albumin) utilized for the development of NS-1 myeloma-derived hybridomas in serum-free media. The medium of the present invention utilizes a single basal medium (IMDM) and a single protein supplement (human transferrin). This sole protein source is a small, well characterized, and easily purified molecule.

Golde, U.S. Pat. No. 4,438,032 describes a human T-lymphoblast cell line (Mo) that, while preferentially grown in a 20% FCS medium, is said to be capable of growth, at a considerably slower rate, in serum-free medium. Nor does he teach use of this cell line as a fusion partner in construction hybridomas.

Galfre, U.S. Pat. No. 4,350,683 describes rat myeloma cell line CNCM I-078, said to be capable of growth in serum free IMDM. He teaches that his cell line may be useful in the development of rat-rat hybridomas. There is no reference to transferring as a sole protein source.

Lundak, EP Appl. No. 62,409 describes a lymphoblastoid cell line capable of growth in serum-free Iscove's medium. This cell line is promoted as a fusion partner for use in hybridoma construction. However, the hybridomas were constructed in a serum-containing medium. Additionally, the parent cell line was grown in a medium which, although serum-free, was conditioned with insulin. Similarly, Chang et al., J. Immunol. Meth. 39:369–75 (1980), describe growth of hybridoma cell lines in serum-free media containing insulin in addition to transferrin.

Transferrins are iron-binding vertebrate proteins. Their nomenclature is rather inconsistent, as noted by Bezkorovainy and Zschocke, Arzheim-Forsch. (Drug Res.) 24:476–485 (No. 4, 1974), and references to "transferrins" are intended to encompass all iron-binding proteins of the transferring class, however derived, unless a specific transferring is clearly indicated.

Tormey, et al., Exper. Cell Res., 74:163–169 (1972) identified transferrin, a constituent of human serum, as a lymphocyte growth promoter. Earlier, Vogt, et al., Exper. Cell Res., 54:195–200 (1969) had reported that the transferring in fetal bovine serum potentiated DNA synthesis in cultured mouse spleen cells.

Hayashi and Sato taught, Nature, 359:132–134 (1976), that the primary role of serum in cell culture is to provide hormones, and that an established rat pituitary cell line could be grown in a serum free medium supplemented with thyrotropin-releasing hormone, transferrin, the biologically active peptide of parathyroid hormone, nd a partially purified somatomedin preparation.

Guilbert and Iscove first found that serum could be partially replaced by Selenite, transferrin, albumin and lecithin in hematopoietic cell cultures. Nature, 263:594–595 (1976). Later, they achieved complete replacement of serum by albumin, transferring and soybean lipid in cultures of liposaccharide-reactive B lymphocytes. In their view, the role of serum is confined "mainly and perhaps entirely to supplying transferrin, lipid and albumin to the cells." J. Exper. Med., 147:923–933 (1978).

Ventrex, in a 1984 circular (SL 001 1/84) on HL-1, "Completely Defined Serum Free Media," states that "for myeloma to grow in HL-1, Supplemental Fetal Bovine Sera . . . must be added." A 0.5% to 1.0% FBS supplement is recommended for P3x63/Ag8.653 derivatives. HL-1 itself contains insulin in addition to transferrin.

Other references of interest are Cartaya, U.S. Pat. No. Re. 30,985, and Moldenhauer, U.S. Pat. No. 4,282,326.

SUMMARY OF THE INVENTION

I have developed a mouse myeloma cell line, adapted to serum-free media, that may be used to construct antibody-secreting hydridomas in serum-free media. Because of the absence of serum proteins, the monoclonal antibodies produced are easy to purify or assay. The expense of serum supplementation is also avoided. The cell line may be of particular advantage to foreign companies because it is possible that they will more readily obtain USDA approval for entry of derivative lines. USDA is concerned with preventing the introduction of Hoof and Mouth Disease into this country by imported fetal calf serum in culture media. If the monoclonal antibodies produced by hybridoma cell lines are to be administered to humans, the problem of bovine serum contamination with non-cytopathogenic bovine viral diarrhea virus must be dealt with. Unfortunately, existing assay, removal and inactivation techniques are not totally reliable.

In order to obtain acceptable growth and secretion levels, others have added a variety of protein supplements to their serum-free media. Unless these proteins are well characterized and easily separated, the aforementioned advantages of serum-free media will not be fully realized.

One object of the invention is to provide a myeloma cell line adapted to grow in a serum-free medium in which transferrin, a well characterized and easily purified molecule, is the sole protein component.

Another object of the invention is to facilitate the construction of monoclonal antibody-secreting hybridomas in such media.

Another object of the invention is to facilitate the separation of monoclonal antibodies from the medium in which they are produced.

Another object of the invention is to reduce the cost of media for hybridoma cell lines.

Another object of the invention is to facilitate assays for monoclonal antibody reactivity by eliminating known interfering substances from the growth medium.

Another object of the invention is to facilitate the importation of hybridoma cell lines.

Other objects of the invention will be apparent to persons having ordinary skill in the art after consideration of the specification and drawings constituting this disclosure.

DETAILED DESCRIPTION OF THE PREFERRED EMBODIMENTS

The mouse myeloma cell line, P3-X63-Ag8.653 (reported by Kearney), is routinely cultured in several types of growth media; for example, Dulbecco's Modified Eagles Medium (D-MEM), Roswell Park Memorial Institute—1640 (RPMI-1640), and Iscove's Modified Dulbecco's Medium (IMDM). All are usually supplmented with 5%–20% fetal bovine serum, horse serum, or calf serum together with other additives such as bovine serum albumin, growth factors, mixtures of lipids and/or fatty acids, transferring, insulin, and various trace elements.

Development of HAZ653-SF

Myeloma cells were initially cultured in Iscoves' Modified Dulbecco's Medium, Iscove and Melchers, J. Exper. Med., 147:923–928, supplemented wtih glutamine, sodium pyruvate, and 10% fetal bovine serum. Over a period of approximately six weeks, the cells were adapted to serum-free growth conditions by serial reduction of serum and supplementation of the medium with 50 ug/ml of human transferrin. Throughout the adaptation process, the myeloma cells were maintained in 8-Azaguanine at $10^{-4}$ M to preserve their sensitivity to HAT. After several passages in the defined medium, the cell line was cloned by limited cell dilution in order to isolate a clonal population with a fixed growth rate. Growth curves for parent and adapted lines are shown in FIG. 1.

The final serum-free medium is IMDM with the following supplements:

| | |
|---|---|
| L-glutamine | 292.0 mg/L |
| Sodium pyruvate | 110.0 |
| Hu Transferrin | 3.3 |
| Penicillin/Streptomycin | 100.0 (optional) |

CONSTRUCTION AND EXAMINATION OF HYBRIDOMAS

Spleen cells for the initial experiments were taken from mice immunized with thyroglobulin, a high molecular weight protein (660,000 daltons) that we have found to be very immunogenic in Balb/c mice. Biweekly sub-cutaneous immunizations, using Freund's adjuvant, resulted in serum titers of 1:150,000 in solid-phase assay. The final boost, 3 days prior to fusion, was administered intravenously. Spleens from immunized mice were removed, minced, and washed 3 times in IMDM containing 2X Pen-Strep. The speen cells were counted and divided equally into 2 tubes. The parent myeloma cells or the adapted cells were added to a final ratio of 4:1 (spleens to myelomas). Concurrent PEG mediated fusions were accomplished and the resultant hybrids were plated into 60 wells of 96-well Costar plates. Serum-containing or serum-free media, each containing HAT, were added to appropriate cultures and plates were incubated at 37° C. in 95%–5% air to $C_2$ atmosphere. Plates were fed at day 5 and day 10 with their respective media, containing HAT. All wells were scored for growth of hybrid colonies on day 11. The data is summarized in Table II.

As can be seen, hybrid colonies were detected in a large percentage of the wells seeded. ELISA assays were used to evaluate immunoglobulin secretion, and although present at variable levels, murine Ig was detected in virtually all of the hybrid-containing wells.

Other experiments were run using spleen cells from mice immunized with a smaller (20,000 dalton), less immunogenic (titer 1:10,000) compound, human placental lactogen. Again, hybrids were detected in a majority of the wells seeded and murine Ig was detected in virtually all hybrid-containing wells (Table I).

In conclusion, the mouse myeloma cell line P3-X63-Ag8.653 was adapted to grow in serum-free, chemically defined media with a transferrin as the sole protein component. The adapted cell line, HAZ653-SF, may be used as a fusion partner to construct and maintain hybridomas in similar, serum-free media. Monoclonal antibodies secreted by the hybrid cells are more easily isolated because of the absence of interfering proteins from the medium. Additionally, there is less risk of cell line contamination by organisms commonly found in sera.

Cell line HAZ653-SF was deposited in the American Type Culture Collection as Myeloma Cell Line 653-SF, ATCC No. CRL8714, on Feb. 1, 1985, under the Budapest Treaty. The deposit of this cell line should not be construed as a license to infringe the claims hereunder.

The parent cell line, P3-X63-Ag8.653, is described in Kearney, et al., J. Immunol. 123:1548–1550 (1979) and is on deposit with the ATCC as CRL 1580.

The grandparent cell line, P3-X63-Ag8, is described in Koprowski, et al., PNAS (USA) 74:2985–2988 (1977), on deposit with ATCC as TIB 9.

TABLE 1

Fusions of 653-SF and Splenocytes from Mice Immunized with Human Placental Lactogen (HPL)

| Fusion | # Splenocytes | # 653 | # Wells Plated | # Cells Well | # Wells w/Growth | # Wells Assayed | # Wells Secreting IgG | # Wells Positive for Antigen | % of Wells Positive | # of Wells Cloned |
|---|---|---|---|---|---|---|---|---|---|---|
| With 10% FBS | $1.1 \times 10^8$ | $2.8 \times 10^7$ | 480 | $5.8 \times 10^5$ | 419 | 419 | 100% | 32 | 8 | 3 |
| Without FBS | $1.1 \times 10^8$ | $2.8 \times 10^7$ | 480 | $5.8 \times 10^5$ | 270 | 270 | 100% | 8 | 3 | 1 |

TABLE 2

Fusions of 653-SF and Splenocytes from Mice Immunized with Bovine Thyroglobulin (BT)

| Fusion | # Splenocytes | # 653 | # Wells Plated | # Cells Well | # Wells w/Growth | # Wells Assayed | # Wells Secreting IgG | # Wells Positive for Antigen | % of Wells Positive | # of Wells Cloned |
|---|---|---|---|---|---|---|---|---|---|---|
| With 10% FBS | $3.7 \times 10^8$ | $8.6 \times 10^7$ | 660 | $6 \times 10^5$ | 507 | 458 | 100% | 431 | 94 | 7 |
| Without FBS | $3.7 \times 10^8$ | $9 \times 10^7$ | 720 | $6 \times 10^5$ | 667 | 235 | 100% | 233 | 99 | 3 |

I claim:

1. A cell line having the identifying characteristics of Myeloma Cell Line HAZ653-SF, ATCC CRL8714, and any cell lines derived therefrom.

2. A method of constructing a hybridoma that comprises (a) providing belonging to a cell line according to claim 1 which is adapted to serum-free media, and (b) fusing them with immunocytes in serum free media.

* * * * *